United States Patent
Granados et al.

(10) Patent No.: US 11,941,837 B2
(45) Date of Patent: Mar. 26, 2024

(54) METHOD FOR IDENTIFYING ELECTRODE CONTACTS IMPLANTED INTO THE BRAIN OF A SUBJECT

(71) Applicant: UCL BUSINESS LTD, London (GB)

(72) Inventors: Alejandro Granados, London (GB); Rachel Sparks, London (GB); Sebastien Ourselin, London (GB)

(73) Assignee: UCL BUSINESS LTD, London (GB)

( * ) Notice: Subject to any disclaimer, the term of this patent is extended or adjusted under 35 U.S.C. 154(b) by 730 days.

(21) Appl. No.: 17/051,708

(22) PCT Filed: Apr. 30, 2019

(86) PCT No.: PCT/GB2019/051198
§ 371 (c)(1),
(2) Date: Oct. 29, 2020

(87) PCT Pub. No.: WO2019/211598
PCT Pub. Date: Nov. 7, 2019

(65) Prior Publication Data
US 2021/0125367 A1    Apr. 29, 2021

(30) Foreign Application Priority Data
Apr. 30, 2018    (GB) ..................................... 1807041

(51) Int. Cl.
*G06T 7/30*    (2017.01)
*A61B 5/00*    (2006.01)
(Continued)

(52) U.S. Cl.
CPC .............. *G06T 7/73* (2017.01); *A61B 5/0035* (2013.01); *A61B 5/0042* (2013.01);
(Continued)

(58) Field of Classification Search
CPC ............ G06T 7/136; G06T 7/11; G06T 7/30; G06T 7/66
See application file for complete search history.

(56) References Cited

U.S. PATENT DOCUMENTS

2016/0189382 A1    6/2016    Deepak et al.

FOREIGN PATENT DOCUMENTS

WO    WO-2012135190 A2    10/2012

OTHER PUBLICATIONS

International Search Report and Written Opinion of the International Searching Authority issued in PCT/GB2019/051198, dated Jun. 19, 2019; ISA/GB.
(Continued)

*Primary Examiner* — Sam Bhattacharya
(74) *Attorney, Agent, or Firm* — Harness, Dickey & Pierce, P.L.C.

(57) ABSTRACT

A computer implemented method of identifying contacts of an electrode implanted into the brain of a subject via bolts through the skull of the subject, based on an image of the subject, the method comprising: identifying at least one bolt region of the image corresponding to a bolt; identifying one or more contact regions of the image corresponding to electrode contacts; determining contact regions associated with an identified bolt region by searching for identified contact regions, the search being performed based on a search axis extending from the identified bolt region, the direction of the search axis being determined based on the identified bolt region.

19 Claims, 11 Drawing Sheets

(51) Int. Cl.
 G06T 7/00 (2017.01)
 G06T 7/11 (2017.01)
 G06T 7/136 (2017.01)
 G06T 7/66 (2017.01)
 G06T 7/73 (2017.01)

(52) U.S. Cl.
 CPC .......... *A61B 5/6864* (2013.01); *G06T 7/0012* (2013.01); *G06T 7/11* (2017.01); *G06T 7/136* (2017.01); *G06T 7/30* (2017.01); *G06T 7/66* (2017.01); *G06T 2207/10081* (2013.01); *G06T 2207/10088* (2013.01); *G06T 2207/20212* (2013.01); *G06T 2207/30016* (2013.01); *G06T 2207/30052* (2013.01)

(56) References Cited

OTHER PUBLICATIONS

Anulfo, G., et al: Automatic Segmentation of Deep Intracerebral Electrodes in computed Tomography scans. BMC Bioinformatics 16(99), 1-12 (2015).

Meesters, S., et al: Automated Identification of Intracranial depth Electrodes in Computed Tomography Dta. IEEE 12th Intl Symp on Biomedical Imaging (ISBI) pp. 976-979 (2015).

Blenkmann et al: iElectrodes: A comprehensive Open-Source Toolbox for Depth and Subdural Grid Electrode Localization, Frontiers in Neuroinformtaics, vol. 11 (2017).

Husch, A. et al. PaCER—A Fully Automated Method for Electrode Trajectory and Contact Reconstruction in Deep Brain Stimulation. NeuroImage: Clinical. 2018.

Narizzano, M. et al. SEEG assistant: a 3DSlicer Extension to Support Epilepsy Surgery. BMC Bioinformtaics. 2017.

D'Alvis, T. et al. PyDBS: An Automated Image Processing Workflow for Deep Brain Stimulation Surgery. Int J Cars. 2015.

Cardinale, F. et al. Stereoelectroencephalography: Surgical methodology, safety, and stereotactic application accuracy in 500 Procedures. Neurosurgery. 2013.

Princich, J.P. et al Rapid and efficient localization of depth electrodes and cortical labeling using free and open source medical software in epilepsy surgery candidates. Frontiers in Neuroscience. 2013.

Qin et al. Automatic and Precise Localization and Cortical Labeling of Subdural and Depth Intracranial Electrodes. Frontiers in Neuroinformatics, 2017.

Horn et al. Lead-DBS: A toolbox for deep brain stimulation electrode localizations and visualizations. NeuroImage. 2015.

Horn et al. Lead-DBS v2: Towards a comprehensive pipeline for deep brain stimulation imaging. NeuroImage. 2019.

Hellerbach et al DiODe: Directional Orientation Detection of Segmented Deep Brain Stimulation Leads: A sequential Algorithm Based on CT Imaging. Stereotact Funct Neurosurg. 2018.

Groppe et al. iELVis: An open source MATLAB toolbox for localizing and visualizing human intracranial electrode data. Journal of Neuroscience Methods. 2017.

Lalys et al Analysis of electrode deformations in deep brain stimulation surgery. Int J Cars 2014.

Husch et al. Assessment of Electrode Displacement and Deformation with Respect to Pre-Operative Planning in Deep Brain Stimulation. Bildverarbeitung fur die Medizin. 2015.

METHOD FOR IDENTIFYING ELECTRODE CONTACTS IMPLANTED INTO THE BRAIN OF A SUBJECT

CROSS REFERENCE TO RELATED APPLICATIONS

This application is a U.S. National Phase Application under 35 U.S.C. 371 of International Application No. PCT/GB2019/051198 filed on Apr. 30, 2019 which claims the benefit of priority from Great Britain Patent Application No. 1807041.7 filed on Apr. 30, 2018. The entire disclosures of all of the above applications are incorporated herein by reference.

The present invention relates to a method for identifying electrode contacts implanted into the brain of a subject, based on an image of the subject.

Epilepsy is a disease characterised by an enduring predisposition to generate epileptic seizures and affects 1% of the population. A third of patients develop chronic refractory focal epilepsy and neurosurgery may provide a cure.

Brain imaging is fundamental in a typical neurosurgical evaluation for determining the epileptogenic zone (EZ) with modalities including structural and functional MRI (e.g. T1/T2-w, FLAIR) and PET. If the EZ is not identifiable, invasive electroencephalography (EEG) recordings are performed in the form of stereo-EEG (SEEG) or subdural grid insertion. SEEG is a procedure in which multiple electrodes are stereotactically inserted to identify the seizure onset zone. Accurate placement of electrode contacts is important for safety, interpretation of the recorded electrical signals and subsequent resection planning. Planning of electrode implantation is crucial for avoiding blood vessel damage and subsequent intracranial haemorrhage (which occurs in 1-2% of patients) and automatic computer-assisted multiple trajectory planning tools have been proposed.

However, intraoperatively, entry point (EP) accuracy can be affected by misregistration of the neuronavigation system, inaccurate alignment, and deflection during drilling, whereas target point (TP) errors may be caused by the angle at which the electrode passes through skull, deflection of the electrode at the dura or within the brain, the rigidity of the electrode, and the depth to which a guiding stylet is inserted. Robotic systems have been introduced to improve EP implantation accuracy. However, TP displacement is a major source of error and understanding why and how electrodes bend may help predict final TP positions during surgical planning and improve EZ localisation.

Accordingly, it is necessary to determine post-operatively the location of electrode contacts within the patient's brain. This may be done manually by a trained clinician based on images of the patient. However, this can be very time consuming. In some cases, 15 electrodes may be implanted each having 10 contacts. This means 150 contacts need to be identified and assigned to a specific electrode. This can take several hours.

Computer implemented approaches for determining the location of electrode contacts within the patient's brain have been proposed (Arnulfo, G., et al: Automatic segmentation of deep intracerebral electrodes in computed tomography scans. BMC Bioinformatics 16(99), 1-12 (2015); Meesters, S., et al: Automated identification of intracranial depth electrodes in computed tomography data. IEEE 12th Intl Symp on Biomedical Imaging (ISBI) pp. 976-979 (2015)). However, these approaches rely on pre-operative plans or require manual input as to the type and specification of each electrode implanted. Further, these approaches do not account well for electrode bending or dense arrangements of contacts from multiple electrodes in close proximity. This results in errors such as incorrectly assigned contacts or inaccurate location of contacts.

It is an aim of the present invention to at least partially address the problems discussed above.

An aspect of the invention provides a computer implemented method of identifying contacts of an electrode implanted into the brain of a subject via bolts through the skull of the subject, based on an image of the subject, the method comprising: identifying at least one bolt region of the image corresponding to a bolt; identifying one or more contact regions of the image corresponding to electrode contacts; determining contact regions associated with an identified bolt region by searching for identified contact regions, the search being performed based on a search axis extending from the identified bolt region, the direction of the search axis being determined based on the identified bolt region.

Optionally, the search axis is determined based on a line extending through a first point in a first part of the identified bolt region located outside the head of the subject.

Optionally, the first part of the identified bolt region is determined based on a head region of the image corresponding to the head of the subject.

Optionally, the first point is determined based on a centroid of the first part of the identified bolt region.

Optionally, the centroid is the centre of mass of the first part of the identified bolt region.

Optionally, the line also extends through a second point, the second point being in a second part of the identified bolt region located inside the head of the subject but outside the brain of the subject, or in a contact region closest to the first part of the identified bolt region.

Optionally, the second part of the identified bolt region is determined based on a brain region of the image corresponding to the brain of the subject.

Optionally, the second point is determined based on a centroid of the second part of the identified bolt region or the contact region closest to the first part of the identified bolt region.

Optionally, the centroid is the centre of mass of the second part of the identified bolt region or the contact region closest to the first part of the identified bolt region.

Optionally, contact regions associated with the identified bolt region are determined based on a distance of a given contact region from a Optionally, contact regions are determined to be associated with the identified bolt region if the distance is less than a predetermined threshold.

Optionally, contact regions associated with the bolt region are determined based on the direction of a given contact region from a location on the search axis.

Optionally, contact regions are determined to be associated with the identified bolt region if the direction is within a predetermined range of directions.

Optionally, the search for contact regions is repeatedly performed at multiple locations along the search axis.

Optionally, the step of determining contact regions associated with an identified bolt region is performed for each identified bolt region.

Optionally, a contact region not associated with an identified bolt region based on the search is associated with an identified bolt region having a search axis closer to the contact region than a predefined threshold distance. Optionally, the contact region is associated with the bolt region having the closest search axis to the contact region.

Optionally, a contact region is associated with an identified bolt region based on a predicted contact region position, the prediction being based on distances between contact regions previously associated with the identified bolt region. The contact region may be an identified contact region not associated with an identified bolt region based on the search, or a contact region generated by the method (e.g. not identified by the method).

Optionally, the bolt regions and/or contact regions are identified by applying at least one threshold filter to the image.

Optionally, the image is a computed tomography image, a magnetic resonance image or a combination of a computed tomography image and a magnetic resonance image.

Optionally, for the combination of a computed tomography image and a magnetic resonance image, the computed tomography image and the magnetic resonance image are aligned.

A second aspect provides processing apparatus comprising a processor configured to perform the method of the first aspect.

A third aspect provided a computer program product comprising instructions, which when executed by a computer, cause the computer to carry out the method of the first aspect.

A fourth aspect provides storage medium comprising instructions, which when executed by a computer, cause the computer to carry out the method the first aspect.

A fifth aspect provides a method of measuring the brain activity of a subject using at least one electrode implanted into the brain of the subject via respective bolts through the skull of the subject, at least one electrode comprising one or more contacts, the method comprising: obtaining an image of the subject; identifying the contacts from the image using the method of the first aspect; recording at least one electrical signal from the one or more contacts.

Optionally, the method of the fifth aspect further comprises: implanting at least one electrode into the brain of the subject via respective bolts in the skull of the subject.

Optionally, the method of the fifth aspect further comprises: correlating the identified contacts with at least one recorded electrical signal.

Optionally, the method of the fifth aspect further comprises determining the location of abnormal brain activity based on the correlated identified contacts and at least one recorded electrical signal.

Optional, the method of the fifth aspect wherein the abnormal brain activity is indicative of epileptic seizures.

Further features of the present invention will be described below by way of non-limiting examples, with reference to the accompanying drawings, in which.

Figure 8:
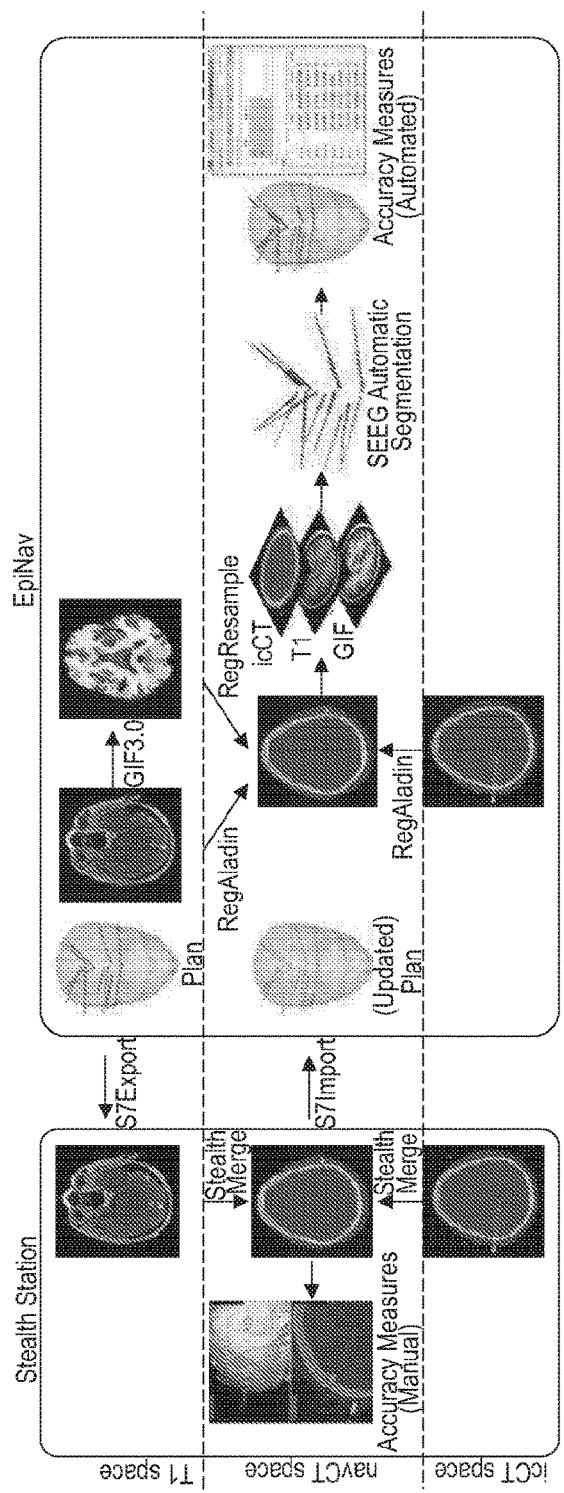

FIG. 8: SEEG Electrode Implantation Assessment Workflow T1-weighted MRI (T1), navigation CT (navCT) and post-implantation CT (icCT) images are acquired before, during and after surgery, respectively. An SEEG electrode implantation plan is created in EpiNav™ and exported to the S7 StealthStation™, where it may be updated by the operating neurosurgeon just before surgery. In the standard clinical workflow accuracy measures are computed manually on the S7 StealthStation™ in the navCT space. EpiNav™ is used to compute accuracy measures automatically, where co-registration of the T1 and icCT to the navCT is performed (NiftyReg) before automatically segmenting SEEG electrodes.

Figure 9:
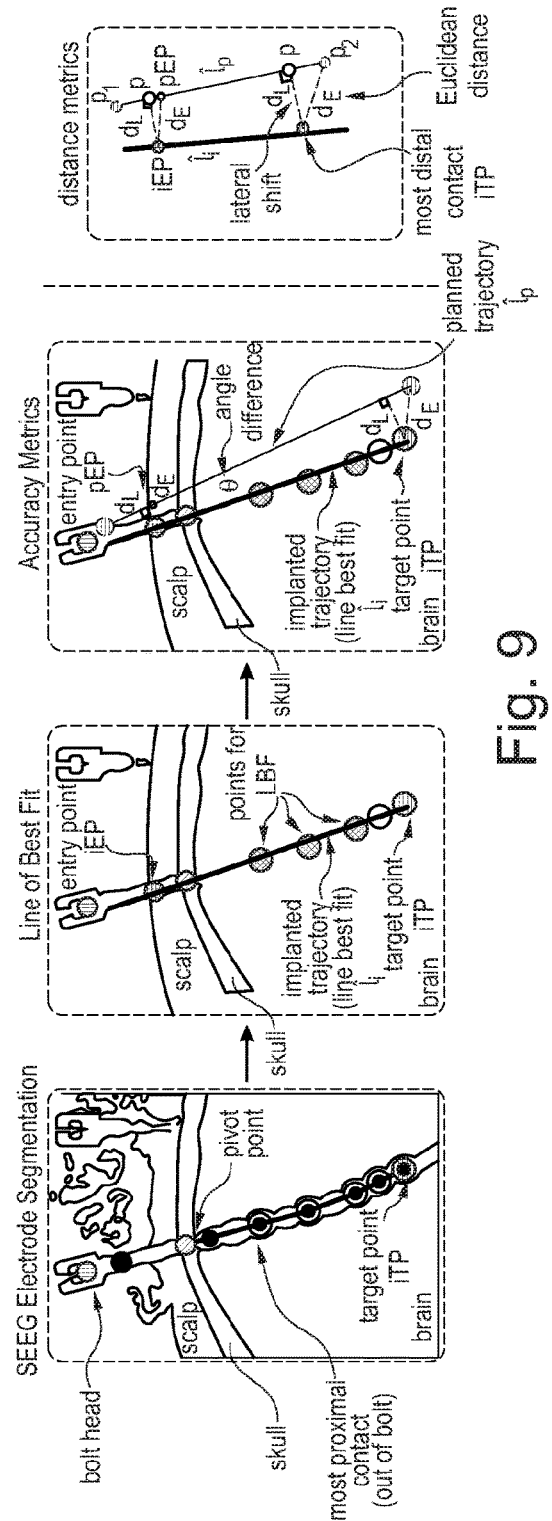

FIG. 9: Estimation of SEEG electrode implantation accuracy measures. Left: automated segmentation of SEEG electrodes identifies the position of the bolt head (green circle) and pivot point (blue circle) and the position of contacts out of the bolt. Centre: A line of best fit (LBF) is computed for a number of contacts (red circles) and used to compute the position of the implanted entry point (iEP—yellow circle) as the collision point between the LBF and a 3Dmesh of the scalp. Right: entry point and target point localisation errors (either as Euclidean dE or lateral dL deviations) and angle difference θ between implanted ($\widehat{li}$) and planned ($\widehat{lp}$) trajectories are computed. Right panel: Details of how distance metrics are computed.

Figure 10:
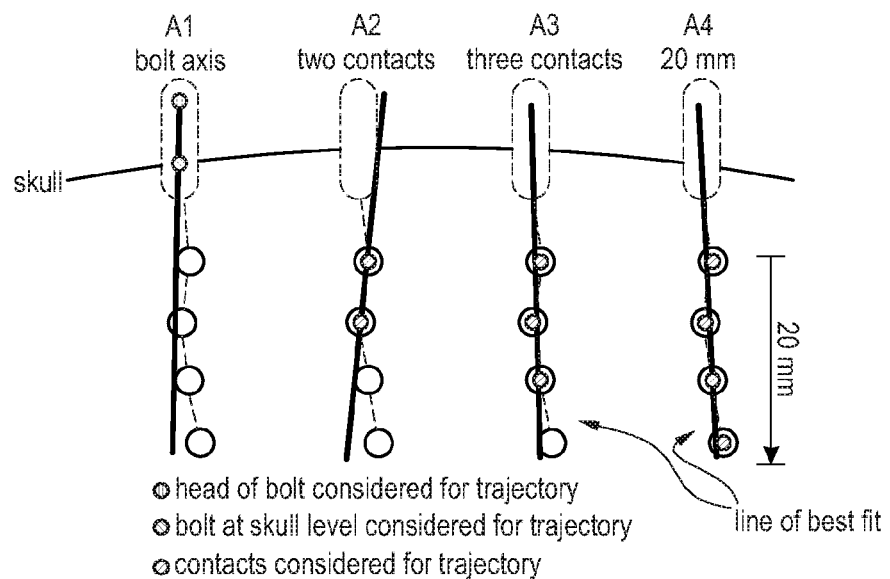

FIG. 10: Four approaches for computing the LBF that take into account: A1) bolt axis (i.e. bolt head to pivot point at level of skull), A2) two most proximal contacts, A3) three most proximal contacts, and A4) N contacts that are within a threshold distance of 20 mm.

Figure 11:
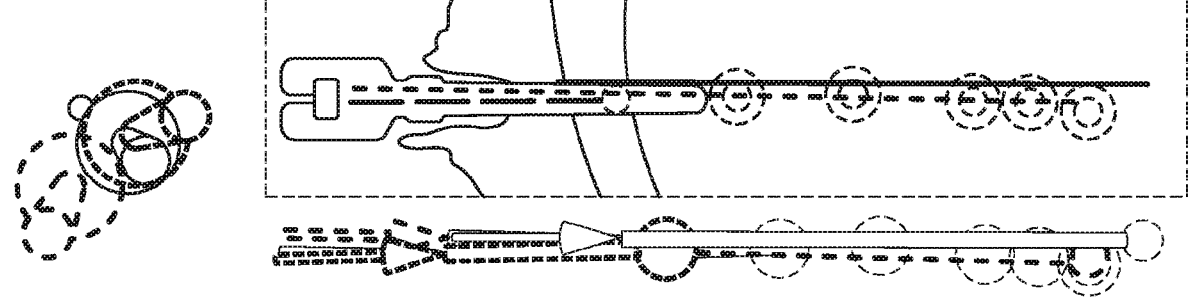

FIG. 11: SEEG electrode trajectories. An example of electrode trajectories including: a) plan (pink), b) automatically segmented electrode (white translucent), c) automatically segmented bolt (blue), and d) line of best fit computed using method 4 (green; FIG. 10). Accuracy metrics: lateral shift at entry point (LE) is 2.107 mm, lateral shift at target point (LT) is 2.342 mm, angle between line of best fit and plan is1.987 degrees.

Figure 12:
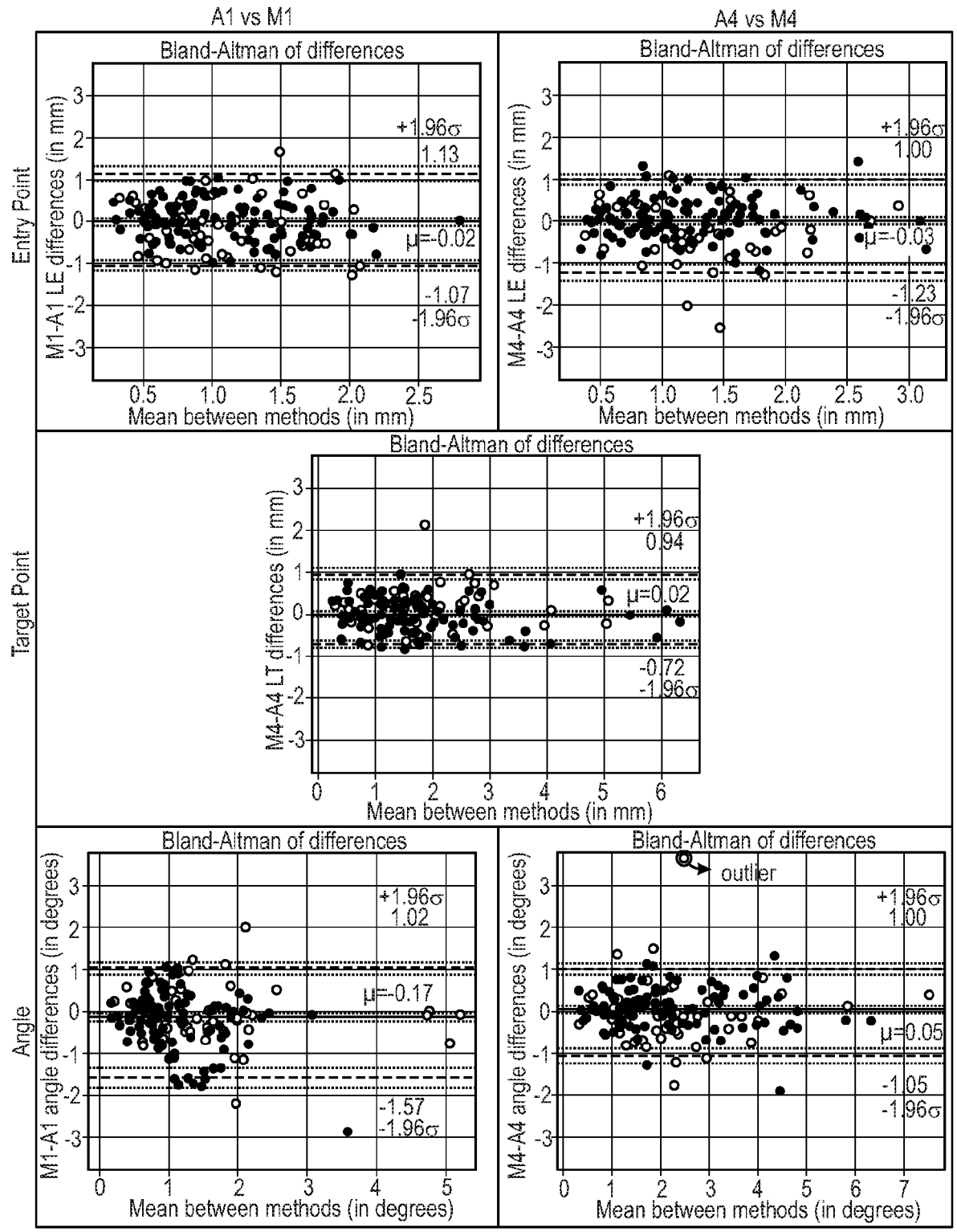

FIG. 12: Validation of accuracy measures between manual and automated approaches (left: M1 vs A1; right: M4 vs A4). Bland-Altman plots of top) LE, middle) LT and bottom) angle difference between planned and implanted trajectories of 158 electrodes. Difference mean (solid line), −1.96 and +1.96 std. dev. (dashed lines), and their confidence interval (dotted lines) are plotted. Electrodes implanted through temporal bone are highlighted in pink.

Figure 13:
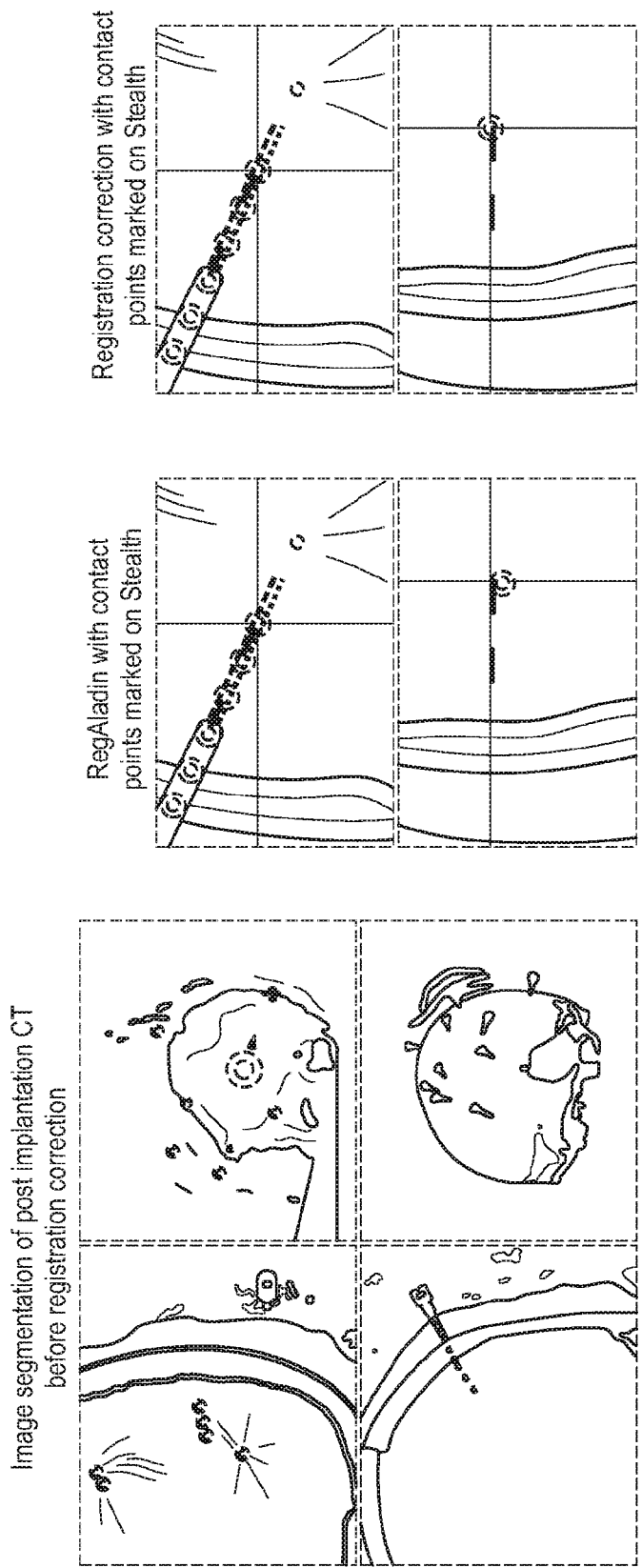

FIG. 13: Registration correction example. Left: Image segmentation of resulting co-registered post-implantation CT from StealthMerge (in red) and RegAladin (in green) before registration. Right: Manually marked contact points overlaid on co-registered post-implantation CT from RegAladin before and after registration correction.

Figure 14:
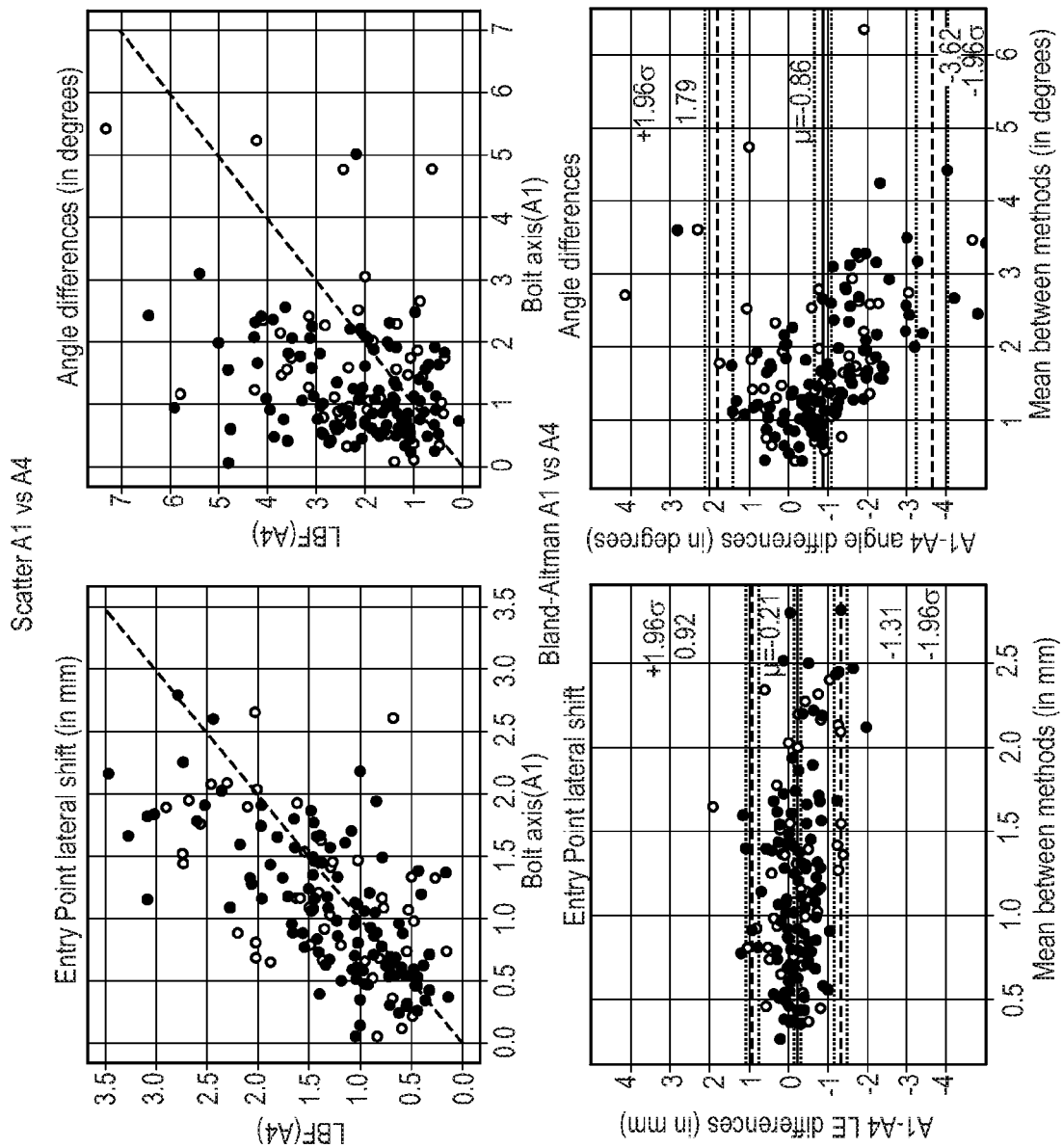

FIG. 14: Comparison between bolt axis (A1) and LBF of contacts up to 20 mm (A4). Scatter top and Bland-Altman bottom plots of LE and angle differences between A1 and A4. Electrodes implanted through temporal bone are highlighted in pink.

Figure 15:
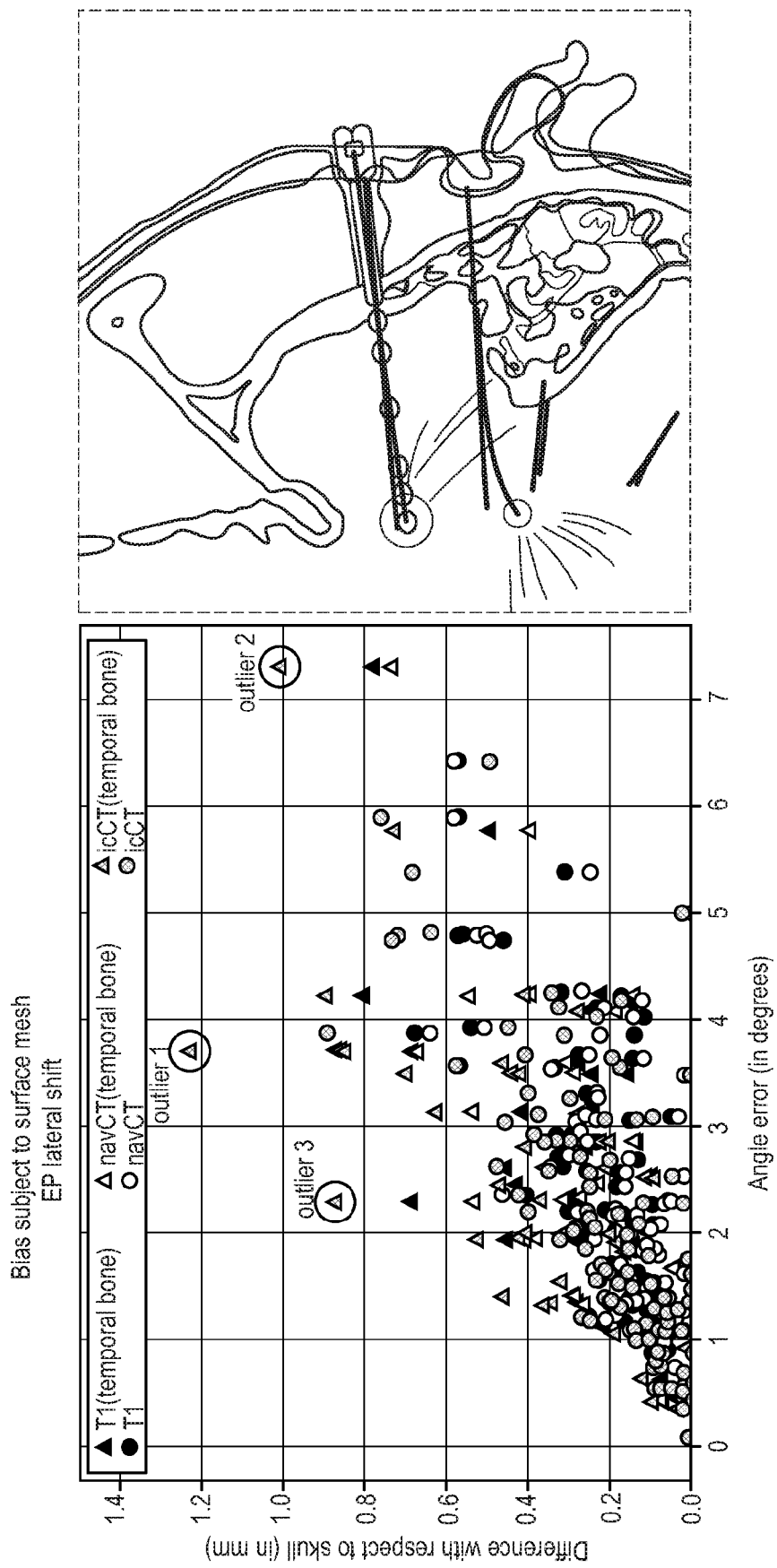

FIG. 15: LE bias subject to surface mesh. Left: Scatter plot of angle error and distance from skull with entry points identified from T1 (red), navCT (yellow) and icCT (green). Electrodes implanted through temporal bone are plotted with triangles. Three outliers are highlighted. Right: Screenshot of electrode trajectory (planned and implanted) related to Outlier 1 outlining skull from navCT (white), and scalp from T1 (red), navCT (yellow) and icCT (green).

Figure 16:
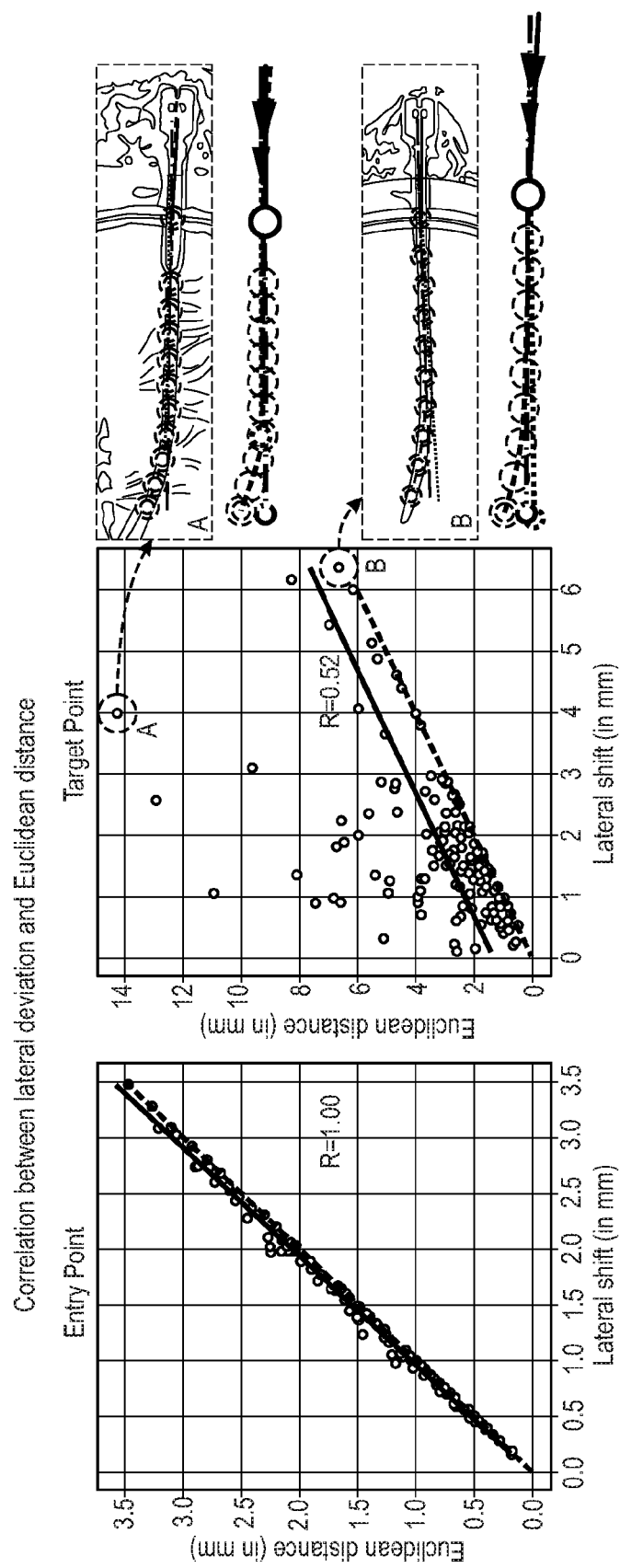

FIG. 16: Correlation between metrics based on lateral shift (LE and LT) and Euclidean distance (EE and ET). Two examples related to target point metrics are highlighted, with one example showing how lateral shift is unable to capture errors in insertion depth of implanted trajectory (in green) compared to planned trajectory (in pink).

Figure 1:
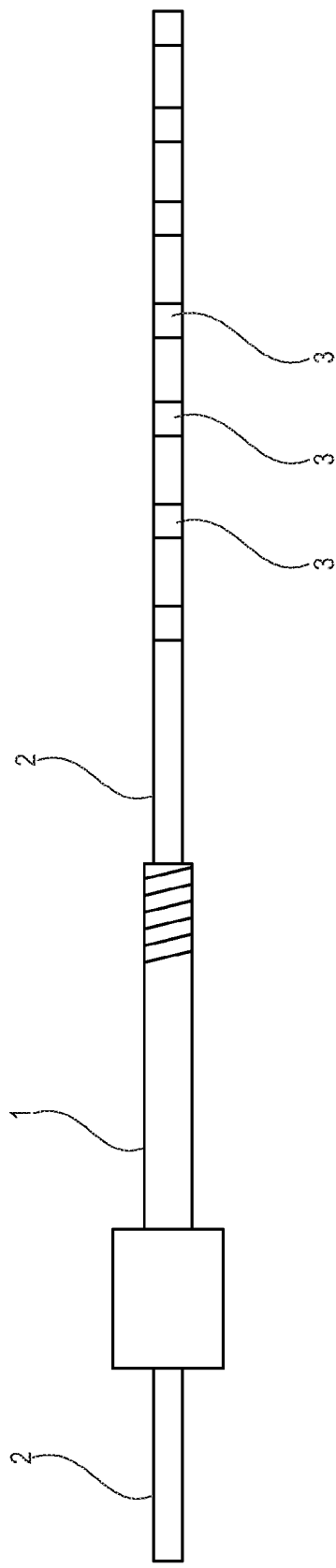
FIG. 1 shows a schematic of a bolt and an electrode inserted through the bolt.

FIG. 1 schematically shows a bolt 1 and electrode 2, such as those typically used in a SEEG procedure. The bolt 1 may have elongate shape and may be made from metal e.g. titanium. The bolt 1 may comprise a threaded portion at a distal end for screwing into the skull of a patient. The bolt 1 may comprise a hollow channel along a longitudinal axis thereof for allowing an electrode 2 to be implanted. The electrode 2 comprises one or more electrode contacts 3 at intervals along the length of the electrode 2. The contacts 3 may be made from metal, e.g. titanium. The portions of the electrodes 2 between the contacts may be made from plastic. When the bolts 1 and electrodes 3 are imaged, e.g. by computed tomography, the bolt 1 and the contacts 3 are visible because they are made from metal, whereas the rest of the electrode 2 is not visible.

An example procedure comprises implanting one or more electrodes into the brain of a subject via respective bolts through the skull of the subject. The bolts provide a channel through the skull to the brain. After the electrodes are inserted, the contacts may be used to measure brain activity by recording electrical signals from the brain. Based on these signals, abnormal brain activity may be determined (e.g. indicative of epileptic seizures). In order to determine the location of the abnormal brain activity, the recorded signals may be correlated with the location of respective contacts in the brain. This may be performed based on images of the subject (e.g. the head of the subject). The images may be obtained any time after implantation of the electrodes. The location of the electrode contacts may be determined at any time after the images are obtained. For example, the images may be obtained before, during or after, the recording of electrical signals.

Figure 2:
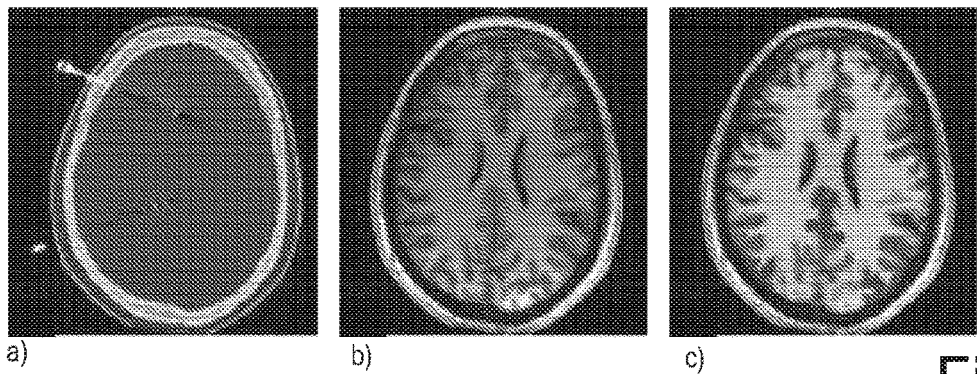
FIG. 2 shows a) a post-implantation CT image, b) a pre-implantation MR image, and c) a parcellation image based on the MR image.

Disclosed herein is a computer implemented method of identifying contacts of an electrode 2 implanted into the brain of a subject via bolts 1 through the skull of the subject, based on an image of the subject. The image may be, for example, a computed tomography (CT) image, a magnetic resonance (MR) image, parcellation image or a combination of a computed tomography image and/or a magnetic resonance image and/or a parcellation image. The combinations of different image modalities may be co-registered (aligned). FIG. 2 shows input images used in an example method, namely a) a post-implantation CT image, b) a pre-implantation MR image, and c) a parcellation image based on the MR image. The parcellation image identifies and labels different anatomical regions of the brain. The images are three-dimensional images, slices through which are shown in FIG. 2.

Various specific regions of the image are identified in the method and specific examples disclosed herein. Identification of these regions is also referred to as segmentation in the art. The identified image areas are also referred to as masks in the art.

The method disclosed herein comprises identifying at least one bolt region of the image corresponding to a bolt, e.g. using image processing. In one example, the bolt regions may be identified by applying a threshold filter (e.g. a binary threshold filter) to an image (e.g. a post-implantation image). The bolt regions may, alternatively or additionally, be identified based on morphological characteristics. For example, regions of the image may be identified as bolt regions based on the total number of pixels in a given region being within a predetermined range, e.g. at least 200 pixels. However, other methods of identifying bolt regions could be used instead.

The method disclosed herein comprises identifying one or more contact regions of the image corresponding to electrode contacts, e.g. using image processing. In one example, the contact regions may be identified by applying a threshold filter (e.g. a binary threshold filter) to an image (e.g. a post-implantation image). The contact regions may, alternatively or additionally, be identified based on morphological characteristics. For example, regions of the image may be identified as contact regions based on the total number of pixels in a given region being within a predetermined range, e.g. between 3 and 50 pixels. However, other methods of identifying bolt regions could be used instead.

Figure 4:
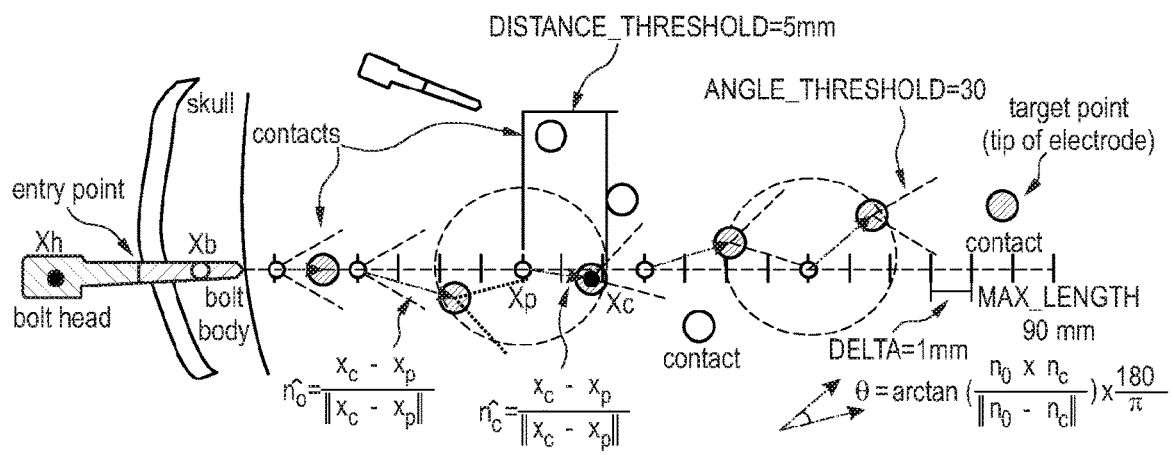
FIG. 4 is a diagram schematically showing an example process for assigning contacts.

The method disclosed herein further comprises determining contact regions associated with an identified bolt region. This is performed by searching for identified contact regions (e.g. contact regions that are likely to be associated with the identified bolt region) based on a search axis extending from the identified bolt region. The direction of the search axis is determined based on the identified bolt region. The search axis may be a reference axis based on which search criteria may be calculated. An example of a search axis is shown in FIG. 4, by the dotted line extending away from the bolt.

The direction of the search axis may correspond to an extension direction of the identified bolt region. The extension direction of the identified bolt region may correspond to the longitudinal axis of the bolt. Preferably, the search axis is determined based only on the image data, i.e. without data about the bolt available pre-operatively.

In an example, the direction of the search axis is determined based on a line extending through a first point (Xh) in a first part (bolt head) of the identified bolt region located outside the head of the subject. The line also extends through a second point. The second point (Xb) may be in a second part (bolt body) of the identified bolt region located inside the head of the subject but outside the brain of the subject. This is shown in FIG. 4. Alternatively, the second point may be in a contact region closest to the first part of the identified bolt region. If, for example, a second part of the bolt region cannot be identified, the second point may be in a contact region closest to the first part of the identified bolt region.

Figure 3:
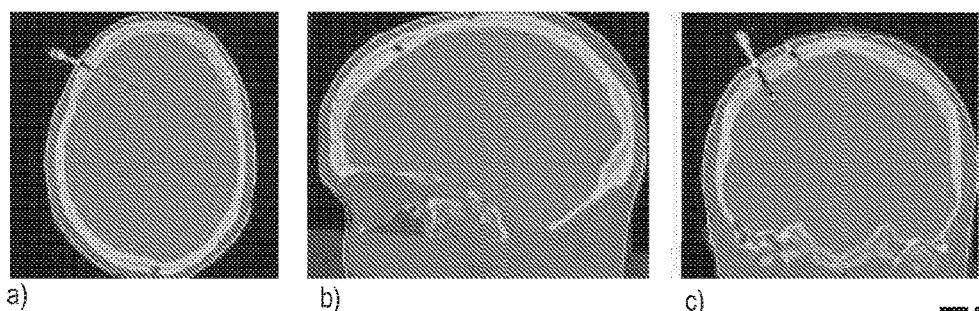
FIG. 3 shows a) axial, b) sagittal and c) coronal planes showing computed masks of the brain, skull and scalp, together with the contacts, the part of the bolt outside the head and the part of the bolt crossing the skull.

The first part of the identified bolt region may be determined based on a head region of the image corresponding to the head of the subject. For example, a part of a bolt region that does not overlap with the head region may be determined to be a first part of the bolt region. The second part of the identified bolt region may be determined based on a brain region of the image corresponding to the brain of the subject. For example, a part of a bolt region that overlaps with a head region but not a brain region may be determined to be a second part of the bolt region. The identified regions, different parts of the bolt regions, and contact regions are shown in FIG. 3.

In an example, a brain region of the image may be identified by applying a threshold filter to the image. A non-brain region may be identified as a region of the image other than the brain region. A threshold filter may be applied to the non-brain region to identify a skull and/or scalp region. The head region may be identified by combining the brain region and the skull and/or scalp region. The brain region, non-brain region, skull and/or scalp region and head region may be identified from a pre-insertion MR image, for example. Different threshold filters may be applied at each of the above stages. At each filtering step, closing filters may additionally be used to close gaps in the image regions. However, other methods may be used to identify the different regions above.

The first point may be determined based on a centroid of the first part of the identified bolt region. The centroid may, for example, be the centre of mass of the first part of the identified bolt region. The second point may be determined based on a centroid of the second part of the identified bolt region or the contact region closest to the first part of the identified bolt region. The centroid may, for example, be the centre of mass of the second part of the identified bolt region or the contact region closest to the first part of the identified bolt region.

Determining contact regions associated with an identified bolt region by searching for identified contact regions based on the search axis, will now be described further, with reference to FIG. 4. The search for contact regions may be repeatedly performed at multiple locations along the search axis, e.g. starting from a location closest to the identified bolt region. The search axis may extend by a predetermined length, at which the searching ends. Search locations are shown by solid lines intersecting the dotted search axis in FIG. 4.

Contact regions associated with the identified bolt region may be determined based on a distance of a given contact region from a location on the search axis. In FIG. 4, contact regions are shown by the larger circles. Contact regions associated with the bolt region are shown as darker than those not associated with the bolt region in FIG. 4.

In an example method, contact regions located within a predetermined distance range from the location along the search axis (e.g. closer than a predetermined distance) may be determined to be associated with the identified bolt region. Search locations from which a contact region is associated with the bolt region are shown by the small circles in FIG. 4. The dashed circles in FIG. 4 show the distance range from example search locations.

Alternatively, or additionally, contact regions associated with the bolt region may be determined based on a direction of a given contact region from a location on the search axis.

In an example, the angle formed between an axis extending between a contact region (e.g. a contact region within the predetermined distance range) and the location along the search axis may be calculated. A contact region may be determined to be associated with the identified bolt region if the angle is within a predetermined range of angles (e.g. less than a predetermined angle). This is shown with reference to the contact region closest to the bolt region in FIG. 4. The arrow from the search location denotes the direction of the search axis. In this case, the associated contact is in line with the search axis.

In another example, the angle formed between an axis extending between a contact region (Xc) and the present location (Xp) along the search axis and an axis extending between a contact region previously associated with the bolt region and a previous location along the axis from which the previously associated contact region was determined, may be calculated. The contact region may be determined to be associated with the identified bolt region if the calculated angle is within a predetermined range of angles (e.g. less than a predetermined angle). As shown at the bottom of FIG. 4 the angle between a present arrow and a previous arrow is calculated. The resulting angular range for the next search location is shown by a dotted cone in FIG. 4. In the case that no previous contact region has been associated with the bolt region, the method of the previous example may be used instead.

Once a given contact region is associated with a bolt region, the given contact region may not then be associated with a different bolt region. In one example, identified but non-associated contact regions may be held in a pool of available contact regions (e.g. labelled as non-associated) and removed from the pool (e.g. labelled as associated) as they are associated with a bolt region. The step of determining contact regions associated with an identified bolt region may be performed for each identified bolt region. For example, the process may continue until all contact regions are associated with a bolt region, or until all contact regions that can be associated with a bolt region are associated with a bolt region.

Contact regions that remain non-associated after any or all of the above searching methods are applied may subsequently be associated with a bolt region by a different method.

For example, a contact region may be associated with bolt region having the closest search axis. For example, the perpendicular (shortest) distance from the contact region to a search axis may be calculated. Only bolt regions having search axes within a predetermined range of distances (e.g. closer than a predetermined distance) may be associated, for example. If more than one bolt region is identified within the distance range, the contact region may be associated with the bolt region having the closest search axis.

Alternatively, or additionally, a bolt region associated with a contact region may be predicted based on parameters of the electrode. For example, the distance between contacts associated with a bolt region may be calculated. Based on this the expected position of a further contact region that may have not been identified (for example, due to its close distance to a bolt region) can be predicted. The further contact region may be an identified contact region that was not associated during the search, or may be a generated contact region. The generated contact region may correspond to a contact that was not identified from the image. For example, the generated contact region may correspond to a contact known to be part of the electrode based on known parameters of the electrode (e.g. number of contacts). The predicted contact region location may be calculated along the search axis between the bolt region and the closest contact region associated with it. The predicted contact region may be associated with the bolt region.

A specific example method is explained below.

Input Images

A post-SEEG implantation resampled CT and an MRI T1 images are rigidly co-registered using NiftyReg (v1.5.43). From the MRI image, the parcellation of brain anatomy was obtained via NiftyWeb (GIF v3.0) (FIG. 2).

Identification of Anatomical Masks

The MRI and the parcellation was used to create regions of interest that are used to identify contacts, bolt heads and the section of the bolt crossing the scalp/skull, which are referred to as bolt body. First, a BinaryThresholdImageFilter is applied to the parcellation to create a mask of intracranial space $B_{Ibrain}$, i.e. with a threshold $t_{brain}$ in the range of $4<t_{brain}<208$. A skull threshold $t_{skull}$ was computed from the MRI as the mean of the intensities of the non-zero voxels that are not brain as an empirical measure to split the low and high intensity regions, followed by a scalp threshold $t_{scalp}$ as the mean of the non-brain voxels above the skull threshold ($VI_{MRI}(x, y, z) > t_{MRIskull}$) to identify the transition between the head and the background.

A BinaryThresholdImageFilter is applied to the MRI to create a mask of the scalp $BI_{scalp}$ with a lower threshold equal to $t_{scalp}$. Morphological operators were used to combine $BI_{brain}$ and $BI_{scalp}$ and apply a closing filter with a ball structuring element (radius=10) to obtain a mask of the head, i.e. $BI_{head}=(BI_{scalp} \cup BI_{brain})$ XOR $B_{10}$, and a mask of the skull, i.e. $BI_{skull}=BI_{head}+BI_{brain}$, after applying an XOR morphological operator on the result (FIG. 3).

Figure 5:
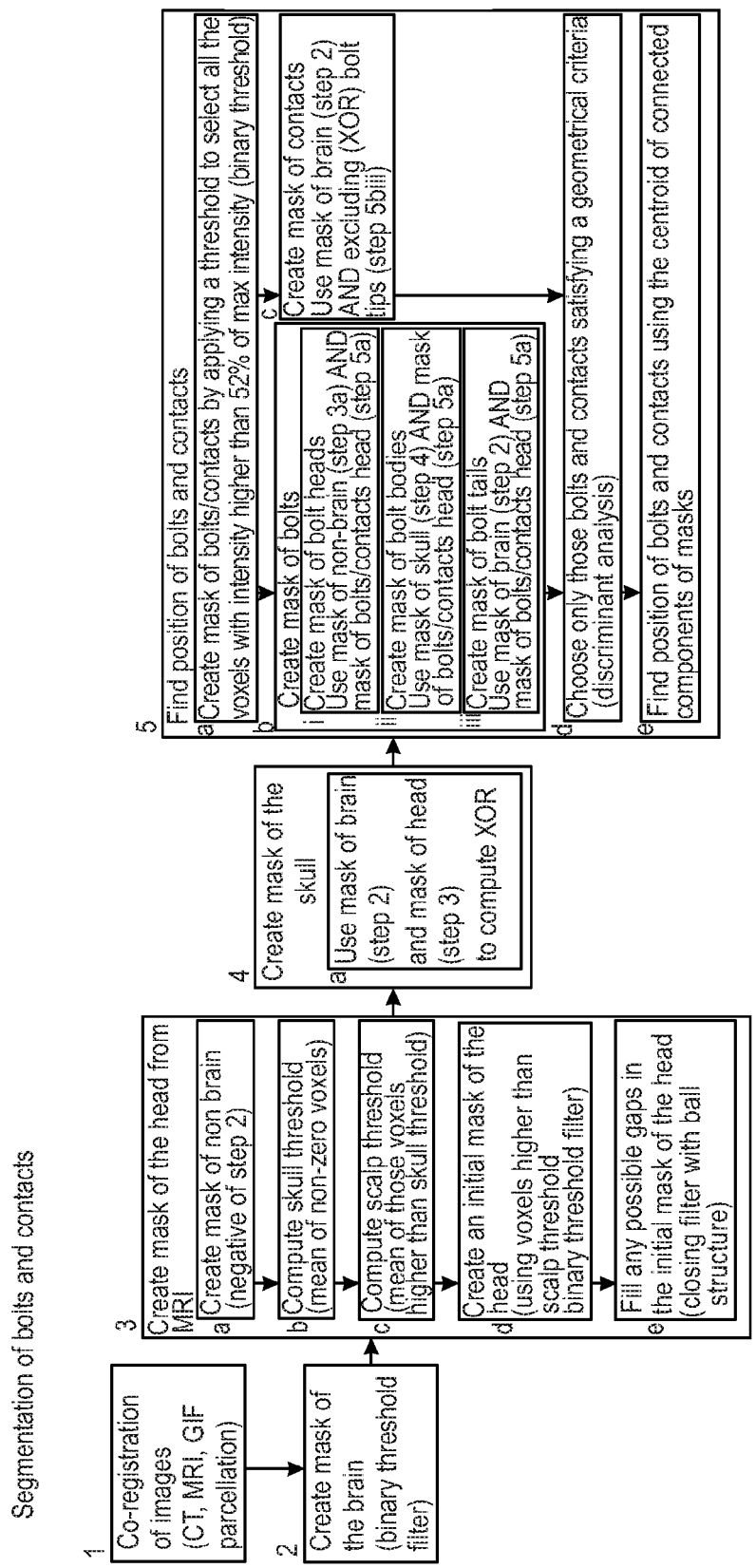
FIG. 5 is a flow chart showing steps of an example process for segmentation.

The above steps are described in the flowchart in FIG. 5.

Segmentation of Electrode Bolts and Contacts

A mask $BI_{post}$ was created from a binary threshold image filter applied to the post-implantation CT image with lower threshold $t_{CT}=(0.52)*\max(I_{CT}(x, y, z))$, i.e. 52% of the maximum image intensity. $BI_{post}$ was used to identify full bolts ($BI_{bolt}$) with at least a minimum of 200 pixels. Three subsections are identified: the head of the bolt which is outside the patient's head ($BI_{bolt} \cap \neg BI_{head}$), the body ($BI_{bolt} \cap BI_{skull}$), i.e. section crossing the skull, and the tip, $BI_{boltTip}$, ($BI_{bolt} \cap BI_{brain}$). Lastly, contacts are identified within the brain whilst excluding bolt tips (($BI_{post} \cap BI_{brain}$) XOR $BI_{boltTip}$). A ConnectedComponentImageFilter was applied to the masks and a LabelImageToShapeLabelMapFilter to the blobs to get their centroids and geometrical properties before conducting geometrical analysis to identify discriminants of segmentation (Table 1).

TABLE 1

Geometrical analysis, μ(σ), and discriminant analysis of bolt heads and contacts.

| | Geometrical analysis | | | Discriminant analysis | |
|---|---|---|---|---|---|
| | Number of Pixels | Elongation | Roundness | Number of pixels | Roundness |
| bolt head | 329.4 (183.5) | 2.51 (0.59) | 0.63 (0.06) | >100 | [0.4, 1.0] |
| contact | 9.7 (6.6) | 2.52 (1.27) | 1.10 (0.06) | [3, 50] | |

Contacts were detected with blobs that were within a range of number of pixels ([3, 50]) and bolt heads with blobs that had a minimum number of pixels (>100) and were within a range of roundness values ([0.4, 1.0]).

The above steps are described in the flowchart in FIG. 5.

Contact Search Strategy

Given a bolt head (xh) and its closest bolt body (xb) positions, the direction of search $$\left(\widehat{n_0} = \frac{xb - xh}{\|xb - xh\|}\right)$$

was computed and a number of points xp given a maximum electrode length (90 mm) and a step size (1 mm) in the direction $\widehat{n_0}$ was iteratively computed. An available contact xc is assigned to the electrode if and only if it is located below a distance constraint from xp (5 mm) and the angle between the previous direction $\widehat{n_0}$ and the current direction $\widehat{n_c}$ is below an angle constraint (30°) (FIG. 4), constraints which favour assigning contacts in the direction of the bolt during a first pass.

Figure 6:
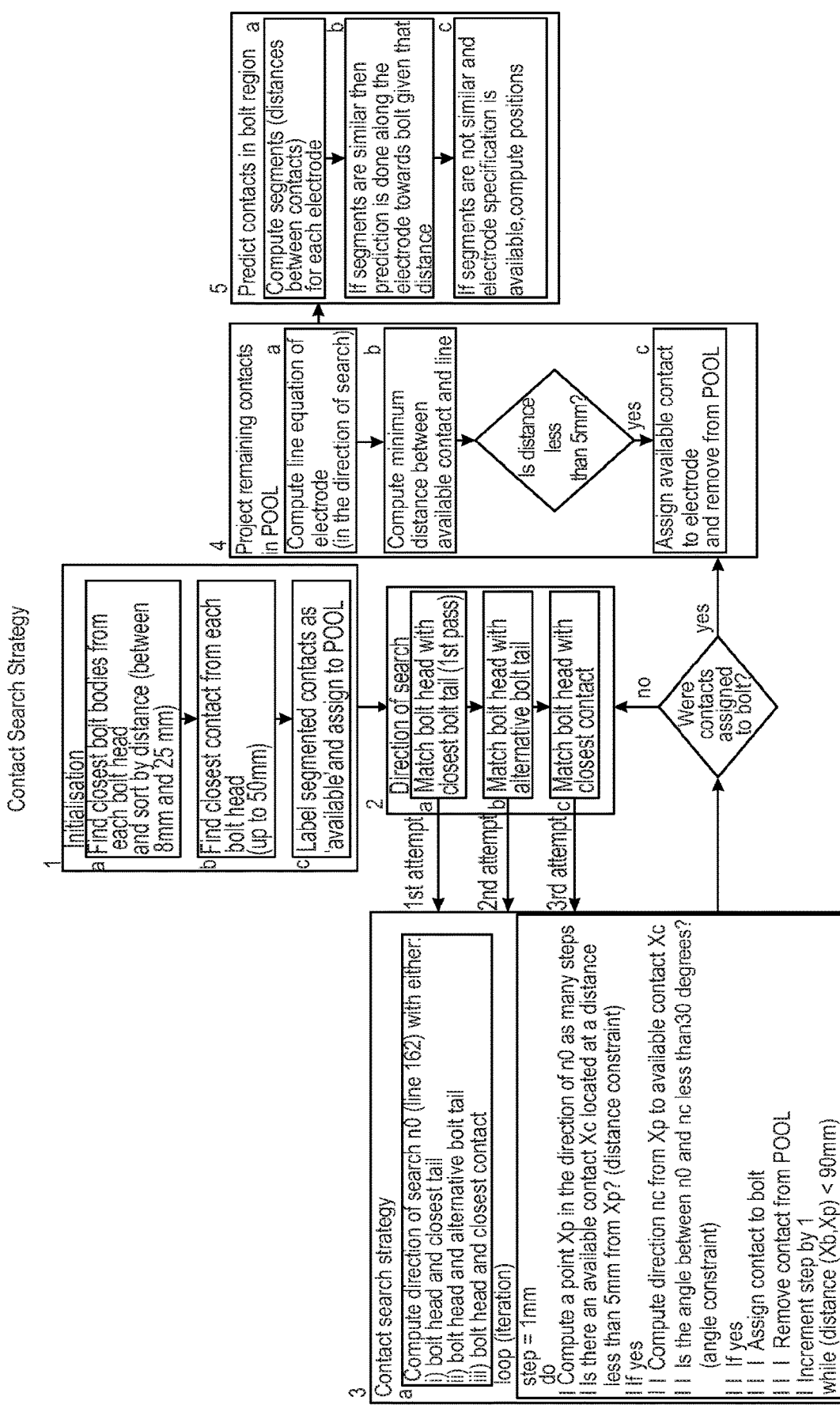
FIG. 6 is a flow chart showing the steps of an example process for assigning contact segments.

The above steps are described in the flowchart in FIG. 6.

Automatic Segmentation of Electrodes

The main steps of the algorithm include:

1. Initialisation. All segmented contacts are initially labelled as 'available' and stored in a pool. Given a bolt head position (xh), the closest bolt bodies (823 $\|xh-xb\|\leq 25$ mm) and the closest contact ($\|xh-xc\|<50$ mm) are identified in order to narrow the search down to only those relevant.

2. Contact search strategy. For each bolt head, the contact search strategy is executed initially with the closest bolt body (1st pass search) and subsequently with alternative bolt bodies if no contacts have been assigned. Although rare, bolt bodies may not be segmented and a direction of search cannot be computed. Therefore, the contact search strategy is called again with the closest contact position rather than a bolt body position.

3. Project remaining contacts in pool. For electrodes containing at least one contact, the minimum distance between an available contact in the pool and a line formed by the positions of the bolt head and the electrode tip is computed. The contact is assigned to the electrode if and only if its distance to the closest point xp to the line (tangent to the line) is below a constraint (5 mm) and xp remains along the line or in a position of the line 20% extended from the tip, i.e. within an interpolation range of [0.0, 1.2] to project contacts that are further from the currently identified tip of the electrode.

4. Predict contacts in the bolt region. For a given electrode, the most common segment along the electrode based on the distances between subsequent contacts rounded to the closest integer is computed. Based on electrode specification the type of electrode depending on the order of the segments and specify contact spacing is inferred. The direction from the last contact xcn towards the bolt head xh and create new contacts up to 21 mm before the bolt head position to segment only those contacts closer to the skull is computed.

The above steps are described in the flowchart in FIG. 6.

Bending Estimation

Figure 7:
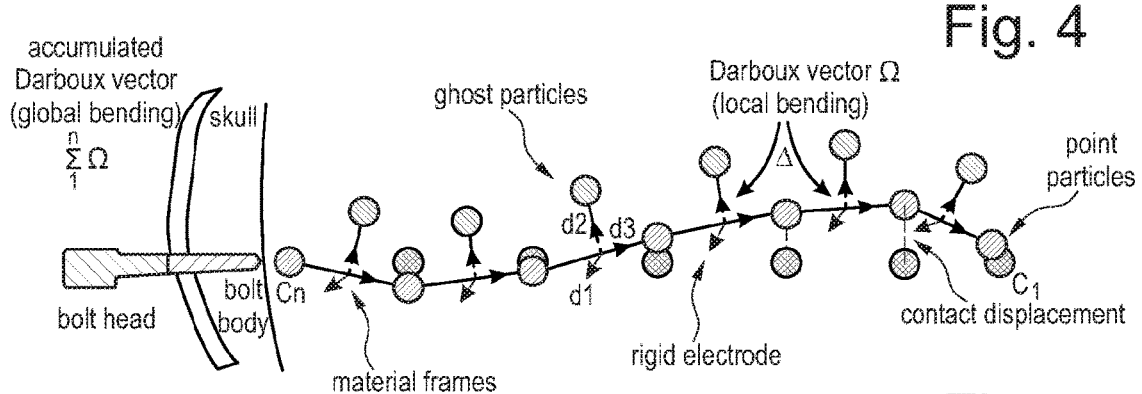
FIG. 7 is a diagram showing an example of electrode bending estimation.

To quantify electrode bending, electrodes are modelled as elastic rods. Electrode contact positions are represented as linked particles with ghost particles located orthogonally half-way between contact pairs (FIG. 7). A material frame is created between contacts with a unit vector $(d_3=x_{C_{n-1}}-X_{C_n})$ aligned tangentially to its centreline followed by two additional orthonormal vectors, $(d_2=\widehat{d_3} \times (X_{C_{n-1}}-X_{C_n})$ and $(d_1=\widehat{d_2} \times \widehat{d_3})$ chosen to lie in the principal direction of the cross section. The rate of change of two consecutive frames, namely a Darboux vector Ω to describe local bending at the contact points is computed. Along the electrode, Ω values are then accumulated to quantify global bending. The parcellation is used to report the region at which each contact is located and report all those regions that the electrode passes through. Lastly, contact displacement and depth are estimated with respect to a rigid electrode with position of contacts projected along the direction from the bolt head to the last contact (Xcn) at distances subject to electrode specification.

Electrode Implantation Quality Assessment

The disclosed method of identifying contacts of an electrode can be extended to provide a method of assessing the quality of electrode implantation. For example, an assessment of quality may be made against a pre-planned electrode trajectory.

Implantation planning can be performed using a T1-weighted MRI (T1) with gadolinium enhancement. Planned trajectories may be exported to a Medtronic, Inc. S7 StealthStation™, the navigation system used in the study. On the day of surgery, bone fiducials are placed into the skull of the patient and a navigation CT (navCT) image is acquired. The T1 may be co-registered to the navCT via StealthMerge™. The operating neurosurgeon then inspects the planned trajectories in the navCT space, and if necessary, makes adjustments. The electrodes are then inserted into the patient as specified by the plan using a frameless system. Within few hours after surgery, a CT (icCT) image is acquired to assess whether the SEEG implantation caused any complications. This post-implantation CT is co-registered to the navCT to determine the location of the implanted electrodes relative to the plan and to calculate implantation accuracy (FIG. 8).

Trajectory Estimation

The trajectory of an electrode may be estimated by defining a line of best fit (LBF) from identified electrode contacts and/or bolts. The LBF may be found for a matrix, M where each row n corresponds to one of N points along the electrode comprising electrode contacts and/or the bolt (see e.g. FIG. 9).

A centroid point c of M (Eq. 1a) may be first computed. D, a matrix describing the contact variation, may be computed by subtracting $\bar{c}$ from M (Eq. 1b). A singular value decomposition (SVD) of D (Eq.1c) may be calculated, where $U \in R^{N \times N}$ and $V \in R^{3 \times 3}$ are the left and right orthogonal singular vectors of D, respectively. The diagonal entries of $\Sigma$ are the singular values ($\sigma_i$) of D, arranged in descending order. The LBF of an electrode implanted trajectory is then defined as:

$$\hat{l}_i = \bar{c} + u_1.$$

where $u_1$ is the entry of U with the corresponding highest singular value in $\Sigma$.

$$\bar{c} = \frac{1}{N}\sum_{n=1}^{N} M_n, : \quad (1a)$$

$$D = M - \bar{c} \quad (1b)$$

$$D = U\Sigma V^T \quad (1c)$$

As shown in FIG. 10, the LBF may be computed using bolt head position and pivot point at skull level (A1: bolt axis), two most proximal electrode contacts (A2), three most proximal contacts (A3), or most proximal contacts within a distance set to 20 mm (A4).

Implanted Entry Point Estimation

A smoothed triangular surface mesh of the scalp, S, may be generated by intensity thresholding of the image followed by morphological closing to ensure a smoothed continuous mesh. The 3D mesh of the scalp may be used to define the implanted entry point (iEP) as the collision point (see FIG. 9) between S and a trajectory line (e.g. a LBF) e.g. via a binary space partitioning (BSP) algorithm (which may be used to improve the computational efficiency of this calculation).

Implanted Target Point Estimation

The position of the most distal contact (i.e. implanted TP–iTP) may be estimated after thresholding of the image (see FIG. 9) followed by computing the centroid of a connected component.

Metric Calculation

Accuracy metrics (entry point error, target point error, and angle difference) may be calculated to measure how well an implanted trajectory, $\hat{l}_i$, adhere to a planned trajectory, $\hat{l}_p$ (FIG. 9)

Lateral distance, is computed as the shortest distance between a point on the implanted trajectory and the planned trajectory. Euclidean distance is the distance of a straight line between a point on the implanted trajectory and a point on the planned trajectory. Lateral distance of entry point (LE) and target point (LT) may be calculated as may Euclidean distance of entry point (EE) and target point (ET).

The angle difference ($\theta$ in degrees) between a planned ($\hat{l}_p$) and implanted trajectory ($\hat{l}_i$) may be computed as $$\theta = \arctan\left(\frac{\|\hat{l}_p \times \hat{l}_i\|}{\hat{l}_p \cdot \hat{l}_i}\right) * \frac{180}{\pi}.$$

Results

FIG. 11 shows an example of a LBF trajectory computed automatically in relation to planned trajectory, automated segmentation of electrode and bolt axis. Given these trajectories, accuracy metrics such as EP, TP and angle difference with respect to planning are computed.

Approaches for LBF

It should be noted that metrics related to TP, i.e. LT and ET, are not affected by the type of implanted trajectory since deviation is measured using the segmentation of the most distal contact (iTP). Overall, it was observed that metrics for A1 (bolt axis) have the lowest mean values and standard deviations, followed by A4 (LBF) (Table 2). Since the inventors observe lower variability in A1 and A4 with respect to other LBF approaches, a comparison with manually computed metrics is presented in the next section.

TABLE 2 comparison of accuracy metrics based on trajectory estimation methods

| | LBF approaches | | | |
|---|---|---|---|---|
| Metrics | A1 | A2 | A3 | A4 |
| EP lateral shift | μ = 1.1 σ = 0.58 | μ = 1.55 σ = 0.82 | μ = 1.38 σ = 0.77 | μ = 1.32 σ = 0.72 |
| Angle Difference | μ = 1.33 σ = 0.95 | μ = 2.75 σ = 1.61 | μ = 2.34 σ = 1.29 | μ = 2.21 σ = 1.33 |

Manual v Automated

Automatically computed metrics related to LE, LT and angle deviations with respect to planned trajectory are compared with those manually done by a clinical scientist. Two implanted trajectory approaches are validated: a) bolt axis (A1), and b) LBF of most superficial contacts outside of the bolt within a 20 mm threshold (A4). The inventors use Box-Cox transformation of metric differences (manual minus automatic) and test for normality using D'Agostino-Pearson test.

Bland-Altman analysis shows no bias of LE metrics computed via an automated approach relative to manual approach, with limits of agreement of [−1.07 1.13] and [−1.23, 1.0] for bolt axis (A1) and LBF of 20 mm (A4), respectively (FIG. 12 top). Similar to the previous section, metrics related to TP are independent of the type of implanted trajectory. The inventors observe no bias in LT with limits of agreement of [−0.72, 0.94], indicating lower variability compared to LE (FIG. 12 middle). Although small, the inventors observe a bias towards the automated approach reporting, on average, 0.17 higher angles than the manual approach using the bolt axis (M1-A1: $\mu=-0.17$; $\sigma=0.67$) with higher limits of agreement of [−1.57, 1.02] compared to those observed for LBF [−1.05, 1.0] (FIG. 12 bottom).

There was found no statistically significant differences in the metrics between automated and manual approaches using a paired non-parametric test (Wilcoxon signed-rank test) with the exception of angle differences using the bolt axis as the implanted trajectory (p=0.0034) (Table. 3). To investigate whether there is an effect of electrodes implanted through temporal bone highlighted in FIG. 12) on the metrics, the inventors use a linear mixed effect model. Fixed effects included electrode length, maximum contact displacement (within a 20.0 mm threshold from most proximal contact out of the bolt) and the interaction of approaches (i.e. manual or automatic) with implanted trajectory (i.e. bolt axis or LFB 20 mm). The inventors considered each patient as a random effect and compare this model with another one that includes temporal bone cases as part of the fixed effects interaction. It was found that electrodes implanted in temporal bone had an effect on angle metrics ($\chi^2=11.237$, p=0.02), increasing it by 0.28 degrees ±0.17 (std. error), with no effect on other metrics. The inventors further investigated potential sources of errors that may have resulted in the differences observed in metrics including differences in registration approaches and number of contacts used to fit the LBF.

the mean average error (MAE) of the contact position from $\mu=0.69$ ($\sigma=0.21$) mm to $\mu=0.28$ ($\sigma=0.17$) mm (FIG. 13). Despite this improvement, the variability between automated and manual approaches of LBF (A4 vs M4) decreased only slightly for LE and LT, although increased for angle deviations (see last column of Table. 3).

Number of Contact Points Used

A large number of electrodes (63.3%) had a different number of contacts (at most one) between manual (M4) and automated (A4) approaches that compute a LBF using contacts within a 20 mm threshold. Differences arise mostly due to round-off errors of automated segmentation and b) partly due to disagreements in defining the most proximal contact out of the bolt. Manually, the clinical scientist determines the number of contact based on contact spacing (electrode specification from the most proximal contact out of the bolt. Our automated approach takes into consideration the Euclidean distance between contact points (from automated segmentation) and the computed distances may be slightly lower/higher (decimal places) than electrode specification. In few cases, there was disagreement in defining the most proximal contact between manual and automated approaches with variability observed when performed manually. However, the inventors found no statistical difference Mann-Whitney U test) in EP (U=2747.00, p=0.29) and angle (U=2853.50, p=0.43) metrics between cases with congruent number of contracts and non-congruent cases between manual and automated approaches.

Bolt Axis Versus LBF

The inventors further studied whether the differences in metrics between trajectories estimated using the bolt axis (A1) and a LBF of proximal contacts within 20 mm (A4)

TABLE 3

Comparison between manual (M) and automated (A) computation of accuracy metrics of two implanted trajectory approaches: a) bolt axis (M1 vs A1) and b) LBF of contacts within a 20 mm threshold (M4 vs A4). Wilcoxon signed-rank test (W) and statistics of differences M − A) are reported. The inventors also report differences when applying an additional transformation to reduce any registration errors as a result of using two different software tools.

|  | Without additional registration | | With additional registration |
|---|---|---|---|
|  | Implanted Trajectory | | |
|  | Bolt axis (A1 vs M1) | LBF of 20.0 mm (A4 vs M4) | LBF of 20.0 mm (A4 vs M4) |
| Entry point lateral shift | W = 6006 (p = 0.64) $\mu = -0.02$ ($\sigma = 0.56$) CI = [−1.07, 1.13] | W = 6061.50 (p = 0.70) $\mu = -0.03$ ($\sigma = 0.58$) CI = [−1.23, 1.00] | W = 5885.00 (p = 0.49) $\mu = -0.03$ ($\sigma = 0.54$) CI = [−1.10, 1.03] |
| Target point lateral shift |  | W = 5944.00 (p = 0.56) $\mu = 0.02$ ($\sigma = 0.43$) CI = [−0.72, 0.94] | W = 5394.00 (p = 0.12) $\mu = 0.05$ ($\sigma = 0.39$) CI = [−0.71, 0.81] |
| Angle difference | W = 4594.50 (p = 0.0034) $\mu = -0.17$ ($\sigma = 0.67$) CI = [−1.57, 1.02] | W = 5715.00 (p = 0.39) $\mu = 0.05$ ($\sigma = 0.60$) CI = [−1.05, 1.00] | W = 5831.00 (p = 0.52) $\mu = 0.04$ ($\sigma = 0.60$) CI = [−1.14, 1.22] |

Registration Error

The inventors assessed the effect differences between manual registration using Stealth-Merge™ on the Medtronic StealthStation, and automated registration, using NiftyReg, had on the LBF computed metrics as follows. Given the position of contacts marked manually on the StealthStation and automatically via SEEG electrode segmentation, the inventors computed a transformation matrix (rotation and translation) to minimise the Euclidian distance between electrode contacts points in the image space. The inventors then applied this transformation to the manual contacts, to better align these points in the navCT space and recomputed the trajectory metrics. This registration correction decreased resulted from electrode bending, which may result in errors calculating A4. The inventors characterise bending by maximum contact displacement of most proximal contacts out of the bolt within a 20 mm threshold. A linear mixed effect model considering maximum contact displacement and trajectory approaches (i.e. A1 and A4) as fixed effects and patient as a random effect indicates that there is an effect on maximum contact displacement (p<0.001) on LE and angle metrics, increasing them by 0.4 mm and 1.45 degrees, respectively. The inventors found also an effect on these metrics when using a LBF, increasing them by 0.05 mm (p<0.01) and 0.22 degrees (p<0.001), respectively. The inventors observe more variability in angle difference metrics using a LBF of 20 mm (A4) compared to a bolt axis (A1) (FIG. 14 top). Bland-Altman analysis shows that, on average, there is a bias of 0.21 mm of LE and 0.86 degree of angle differences towards metrics computed using LBF (A4) (FIG. 14 bottom). There is an increase of variability ([−3.62, 1.79]) of angle differences between A1 and A4 as the size of the data increases and a trend where A1 is bigger than A4 for low mean values between methods, but A1 is lower than A4 for high mean values. The inventors found no effect of electrodes implanted through the temporal bone on metrics when considering maximum contact displacement.

Entry Point Surface

Entry point errors are calculated from the point a trajectory ($\hat{lt}$ or $\hat{lp}$) intersects a Surface mesh S. Angle error θ and distance 1 from the pivot point (at the skull level) will introduce bias in this metric. To estimate this bias, the inventors computed LE for different surface meshes skull from navCT (reference), scalp from T1, scalp from navCT, and scalp from icCT. The inventors found that the differences of LE of a scalp from T1 or navCT, with respect to the LE using the skull, are similar and have the lowest error ($\mu=0.19$; $\sigma=0.17$). The scalp from icCT has the highest error and is statistically significant different to the errors observed for the scalp from T1 ($p=0.0105$) and the scalp from navCT ($p=0.0033$), where p-values have been adjusted following Bonferroni correction (FIG. 15). It should be noted that outliers were observed in electrodes implanted in the temporal bone, a region where the scalp is the thickest.

TABLE 4

Entry point surface errors with respect to skull (navCT) of different scalp surface meshes generated from: T1, navCT and icCT.

| | Image | Mean | Std. Dev. | Significance |
|---|---|---|---|---|
| Scalp | T1 | $\mu = 0.19$ | $\sigma = 0.17$ | T1 vs navCT: p = 0.36 |
| | navCT | $\mu = 0.19$ | $\sigma = 0.17$ | T1 vs icCT: p = 0.003 |
| | icCT | $\mu = 0.25$ | $\sigma = 0.22$ | navCT vs icCT: p = 0.001 |

Lateral Versus Euclidean Distance

The inventors further investigate the correlation between lateral shift and Euclidean-based metrics (FIG. 16). Metrics related to entry point are highly correlated $\rho=1.0$, as both metrics are computed at the intersection of the planned and implanted (LBF) trajectories with the scalp mesh. However, lateral shift distance metrics related to target point are unable to capture errors of electrode insertion depth (with respect to the plan), whereas Euclidean distance metrics do. This is reflected by higher variability between distance metrics and lower correlation when fitting a least squares regression model ($\rho=0.52$). The larger amount of variability observed, by comparison to EP distance metrics, is the result of differences of depth implantation with respect to the plan. Two example electrodes are highlighted: A) the metric based on Euclidean distance reports a much higher error compared to that one based on lateral shift since the implanted trajectory was inserted long from planning (i.e. more than initially planned), and B) both metrics report similar values since insertion depth was similar.

The invention claimed is:

1. A computer implemented method of identifying contacts of an electrode implanted into the brain of a subject via bolts through the skull of the subject, based on an image of the subject, the method comprising:
identifying at least one bolt region of the image corresponding to a bolt;
identifying one or more contact regions of the image corresponding to electrode contacts;
determining contact regions associated with an identified bolt region by searching for identified contact regions, the search being performed based on a search axis extending from the identified bolt region, the direction of the search axis being determined based on the identified bolt region, and the search axis is determined based on a line extending through a first point in a first part of the identified bolt region located outside the head of the subject.

2. The method of claim 1, wherein the first part of the identified bolt region is determined based on a head region of the image corresponding to the head of the subject.

3. The method of claim 1, wherein the first point is determined based on a centroid of the first part of the identified bolt region.

4. The method of claim 3, wherein the centroid is the centre of mass of the first part of the identified bolt region.

5. The method of claim 1, wherein the line also extends through a second point, the second point being in a second part of the identified bolt region located inside the head of the subject but outside the brain of the subject, or in a contact region closest to the first part of the identified bolt region.

6. The method of claim 5, wherein the second part of the identified bolt region is determined based on a brain region of the image corresponding to the brain of the subject.

7. The method of claim 5, wherein the second point is determined based on a centroid of the second part of the identified bolt region or the contact region closest to the first part of the identified bolt region.

8. The method of claim 7, wherein the centroid is the centre of mass of the second part of the identified bolt region or the contact region closest to the first part of the identified bolt region.

9. The method of claim 1, wherein contact regions associated with the identified bolt region are determined based on a distance of a given contact region from a location on the search axis optionally wherein contact regions are determined to be associated with the identified bolt region if the distance is less than a predetermined threshold.

10. The method of claim 1, wherein contact regions associated with the bolt region are determined based on the direction of a given contact region from a location on the search axis optionally wherein contact regions are determined to be associated with the identified bolt region if the direction is within a predetermined range of directions.

11. The method of claim 1, wherein the search for contact regions is repeatedly performed at multiple locations along the search axis.

12. The method of claim 1, wherein the step of determining contact regions associated with an identified bolt region is performed for each identified bolt region.

13. The method of claim 1, wherein a contact region not associated with an identified bolt region based on the search is associated with an identified bolt region having a search axis closer to the contact region than a predefined threshold distance optionally wherein the contact region is associated with the bolt region having the closest search axis to the contact region.

14. The method of claim 1, wherein a contact region is associated with an identified bolt region based on a predicted contact region position, the prediction being based on distances between contact regions previously associated with the identified bolt region.

15. The method of claim 1, wherein the bolt regions and/or contact regions are identified by applying at least one threshold filter to the image.

16. The method of claim 1, wherein the image is a computed tomography image, a magnetic resonance image or a combination of a computed tomography image and a magnetic resonance image wherein for the combination of a computed tomography image and a magnetic resonance image, the computed tomography image and the magnetic resonance image are aligned.

17. A processing apparatus comprising a processor configured to perform the method of claim 1.

18. A computer program product comprising instructions, which when executed by a computer, cause the computer to carry out the method of claim 1.

19. A computer-readable storage medium comprising instructions, which when executed by a computer, cause the computer to carry out the method of claim 1.

* * * * *